United States Patent
Narihata (10) Patent No.: US 12,158,407 B2
(45) Date of Patent: Dec. 3, 2024

(54) FINE-PARTICLE SAMPLING DEVICE HAVING AN ARRANGEMENT OF FIRST AND SECOND ELECTRODES AND METHOD OF SAMPLING FINE PARTICLES

(71) Applicant: Panasonic Intellectual Property Management Co., Ltd., Osaka (JP)

(72) Inventor: Koki Narihata, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 241 days.

(21) Appl. No.: 17/809,281

(22) Filed: Jun. 28, 2022

(65) Prior Publication Data

US 2022/0326135 A1    Oct. 13, 2022

Related U.S. Application Data

(63) Continuation of application No. PCT/JP2020/049223, filed on Dec. 28, 2020.

(30) Foreign Application Priority Data

Jan. 30, 2020    (JP) .................................. 2020-013369

(51) Int. Cl.
    *G01N 15/06*    (2024.01)
(52) U.S. Cl.
    CPC ................................ *G01N 15/0656* (2013.01)
(58) Field of Classification Search
    None
    See application file for complete search history.

(56) References Cited

U.S. PATENT DOCUMENTS

| 4,185,971 | A | 1/1980 | Isahaya | |
|---|---|---|---|---|
| 9,863,855 | B2 * | 1/2018 | Arimoto | ............... G01N 33/497 |

(Continued)

FOREIGN PATENT DOCUMENTS

| CN | 102224404 A | * 10/2011 | ............. B03C 3/014 |
|---|---|---|---|
| EP | 496092 | 7/1992 | |

(Continued)

OTHER PUBLICATIONS

International Search Report of PCT application No. PCT/JP2020/049223 dated Mar. 23, 2021.

*Primary Examiner* — Peter J Macchiarolo
*Assistant Examiner* — Jermaine L Jenkins
(74) *Attorney, Agent, or Firm* — Wenderoth, Lind & Ponack, L.L.P.

(57) ABSTRACT

A fine-particle sampling device for sampling fine particles in a liquid includes a tubular first electrode whose both ends in an axial direction thereof are open; a second electrode extending in the axial direction of the first electrode and disposed in the inside of the first electrode to be spaced from an inner surface of the first electrode; a supplier that supplies a liquid to the inside of the first electrode and causes the liquid to be stored at a portion of the inner surface in a direction around an axis B of the first electrode; a voltage applicator that applies a voltage between the first electrode and the second electrode; a driver that rotates the first electrode around a rotational axis extending in the axial direction of the first electrode and passing through the inside of the first electrode; and a retriever that retrieves the stored liquid.

11 Claims, 7 Drawing Sheets

(56) References Cited

U.S. PATENT DOCUMENTS

| | | | |
|---|---|---|---|
| 10,281,416 B2 * | 5/2019 | Song | G01R 33/307 |
| 10,981,174 B1 * | 4/2021 | Koh | B01L 7/525 |
| 11,927,520 B2 * | 3/2024 | Shkolnikov | G01N 15/0227 |
| 2003/0115975 A1 | 6/2003 | Saaski et al. | |
| 2006/0110818 A1 | 5/2006 | Hill et al. | |
| 2007/0034025 A1 | 2/2007 | Pant et al. | |
| 2017/0138831 A1 | 5/2017 | Okuda et al. | |
| 2018/0275023 A1 | 9/2018 | Skarping et al. | |

FOREIGN PATENT DOCUMENTS

| | | |
|---|---|---|
| JP | 52-166881 U | 12/1977 |
| JP | 54-064777 | 5/1979 |
| JP | 2008-161143 | 7/2008 |
| JP | 2009-011265 | 1/2009 |
| JP | 2012-052866 | 3/2012 |
| JP | 2018-512582 | 5/2018 |
| WO | 2016/002647 | 1/2016 |

\* cited by examiner

FINE-PARTICLE SAMPLING DEVICE HAVING AN ARRANGEMENT OF FIRST AND SECOND ELECTRODES AND METHOD OF SAMPLING FINE PARTICLES

BACKGROUND

1. Technical Field

The present disclosure relates to a fine-particle sampling device that samples fine particles and a method of sampling fine particles.

2. Description of the Related Art

In related art, there are a known device and a known method for sampling fine particles in a gas by using a device utilizing inertia and a centrifugal force of the fine particles (refer to, for example, Japanese Unexamined Patent Application Publication No. 2008-161143, Japanese Unexamined Patent Application Publication No. 2009-11265, and Japanese Unexamined Patent Application Publication No. 2012-52866). Japanese Unexamined Patent Application Publication No. 2008-161143 discloses a method of capturing microbes floating in the air on a membrane filter by sucking the air through the membrane filter. Japanese Unexamined Patent Application Publication No. 2009-11265 discloses an airborne bacteria sampler that causes air that has been taken in through a suction portion to collide with a medium to thereby cause floating bacteria in the air to adhere to the medium and to be caught. Japanese Unexamined Patent Application Publication No. 2012-52866 discloses a device that uses a centrifugal force generated due to a swirl of sucked air to separate and catch a catching object from the air.

SUMMARY

In the aforementioned configurations in related art, however, fine particles of aerosol or the like separated from sucked air are accumulated in a dried state in most cases and require an additional step, such as being extracted into a solution, for analysis. When fine particles to be sampled are living things, it is not possible to catch the living things while maintaining activity thereof. Even when the purpose is retrieve into a solution to solve these problems, a large amount of time is required to obtain a high concentration due to a large amount of the solution, resulting in generation of a large pressure loss due to suction and large noise due to suction. In addition, since the catching performance greatly depends on factors including the shape of the device, the size of the device, suction speed, the size of object aerosol, and the like, there is a problem that catching cannot be performed efficiently.

One non-limiting and exemplary embodiment provides a technology capable of sampling fine particles efficiently.

In one general aspect, the techniques disclosed here feature a fine-particle sampling device that samples fine particles in a liquid, the fine-particle sampling device including: a first electrode having a tubular shape and whose both ends in an axial direction thereof are open; a second electrode extending in the axial direction of the first electrode and disposed in an inside of the first electrode to be spaced from an inner surface of the first electrode; a supplier that supplies a liquid to the inside of the first electrode and causes the liquid to be stored at a portion of the inner surface in a direction around an axis of the first electrode; a voltage applicator that applies a voltage between the first electrode and the second electrode; a driver that rotates the first electrode around a rotational axis extending in the axial direction of the first electrode and passing through the inside of the first electrode; and a retriever that retrieves the stored liquid.

The fine-particle sampling device according to one aspect of the present disclosure can sample fine particles efficiently.

It should be noted that general or specific embodiments may be implemented as a system, a method, an integrated circuit, a computer program, a storage medium, or any selective combination thereof.

Additional advantages and effects of one aspect of the present disclosure will become apparent from the specification and drawings. The advantages and/or effects may be individually provided by the various embodiments and features described in the specification and drawings, which need not all be provided in order to obtain one or more of the same features.

DETAILED DESCRIPTIONS

Hereinafter, embodiments of the present disclosure will be described with reference to the drawings.

Note that a fine-particle sampling device and a method of sampling fine particles according to the present disclosure are not intended to be limited to the embodiments described below and/or to the configurations illustrated in the drawings and include configurations equivalent thereto.

The embodiments described below each indicate comprehensive or specific examples. The numbers, the shapes, the materials, the components, the arrangement positions and connection forms of the components, the steps, the order of the steps, and the like indicated in the following embodiments are examples and are not intended to limit the claims. The drawings are not necessarily exactly illustrated. In the drawings, substantially identical configurations are given identical signs, and overlapping description thereof may be omitted or simplified.

In the following, terms, such as parallel and perpendicular, indicating relationships among components, terms, such as a cylindrical shape, indicating shapes of components, and numerical value ranges not only indicate strict meanings but also mean that substantially equivalent ranges, for example, differences of about several percent are included.

In the following drawings, the X-axis and the Y-axis are axes orthogonal to each other on a horizontal plane. The Z-axis is an axis perpendicular to a horizontal plane. In the Z-axis, the positive direction indicates the vertically upward direction, and the negative direction indicates the vertically downward direction.

Embodiment

Figure 1:
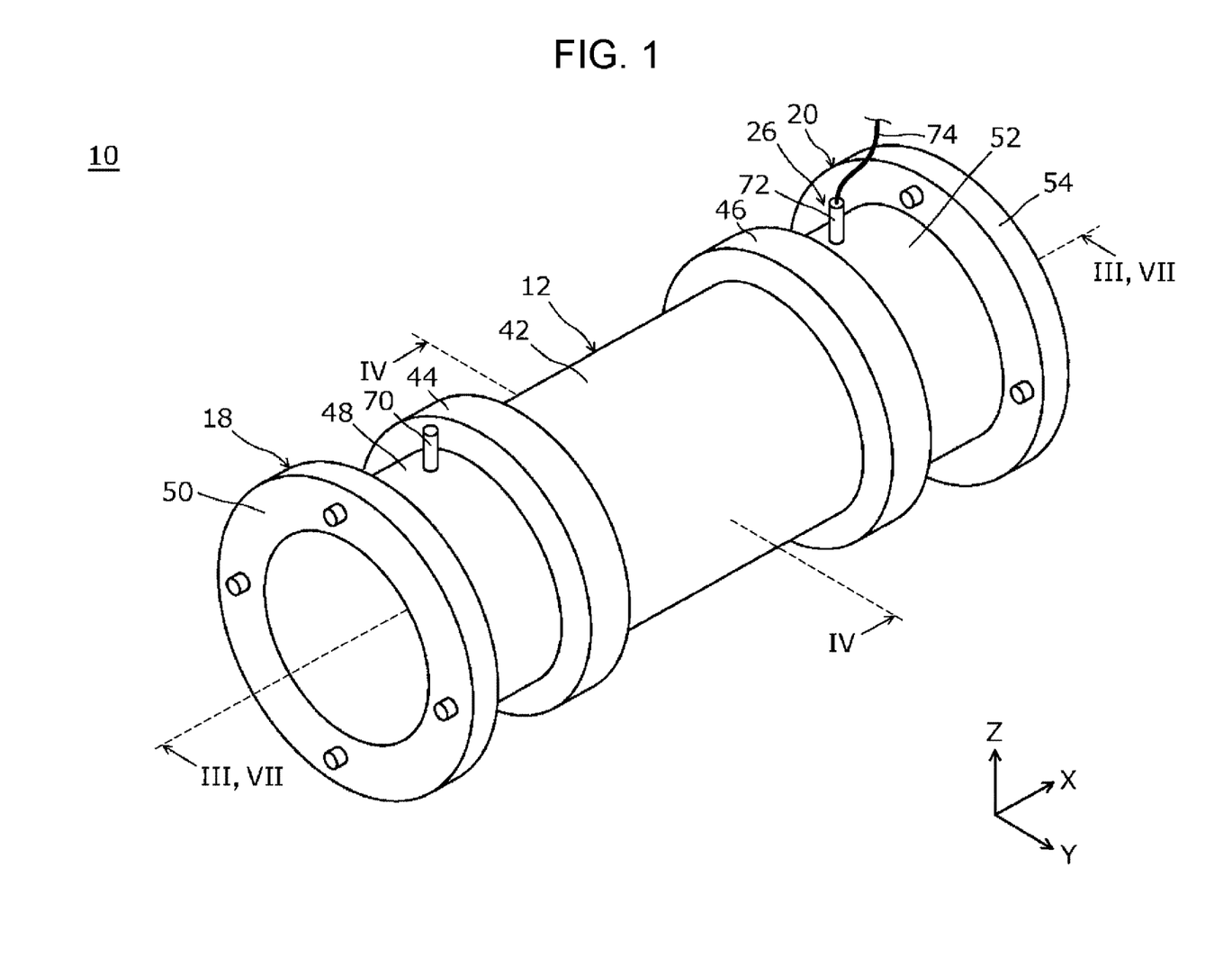
FIG. 1 is a perspective view illustrating an appearance of a fine-particle sampling device according to an embodiment.
Figure 2:
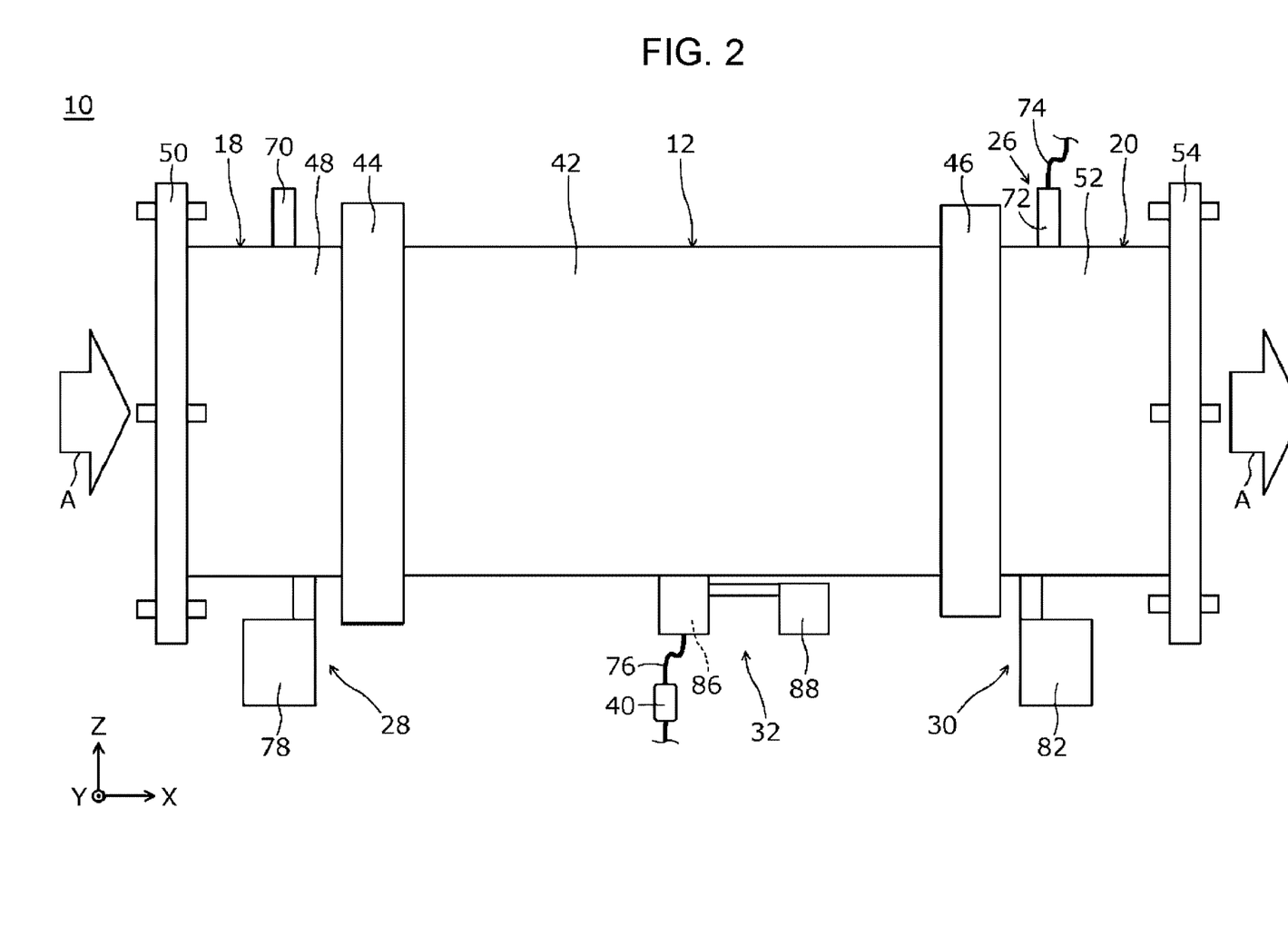
FIG. 2 is a side view illustrating an appearance of the fine-particle sampling device in FIG. 1.
Figure 3:
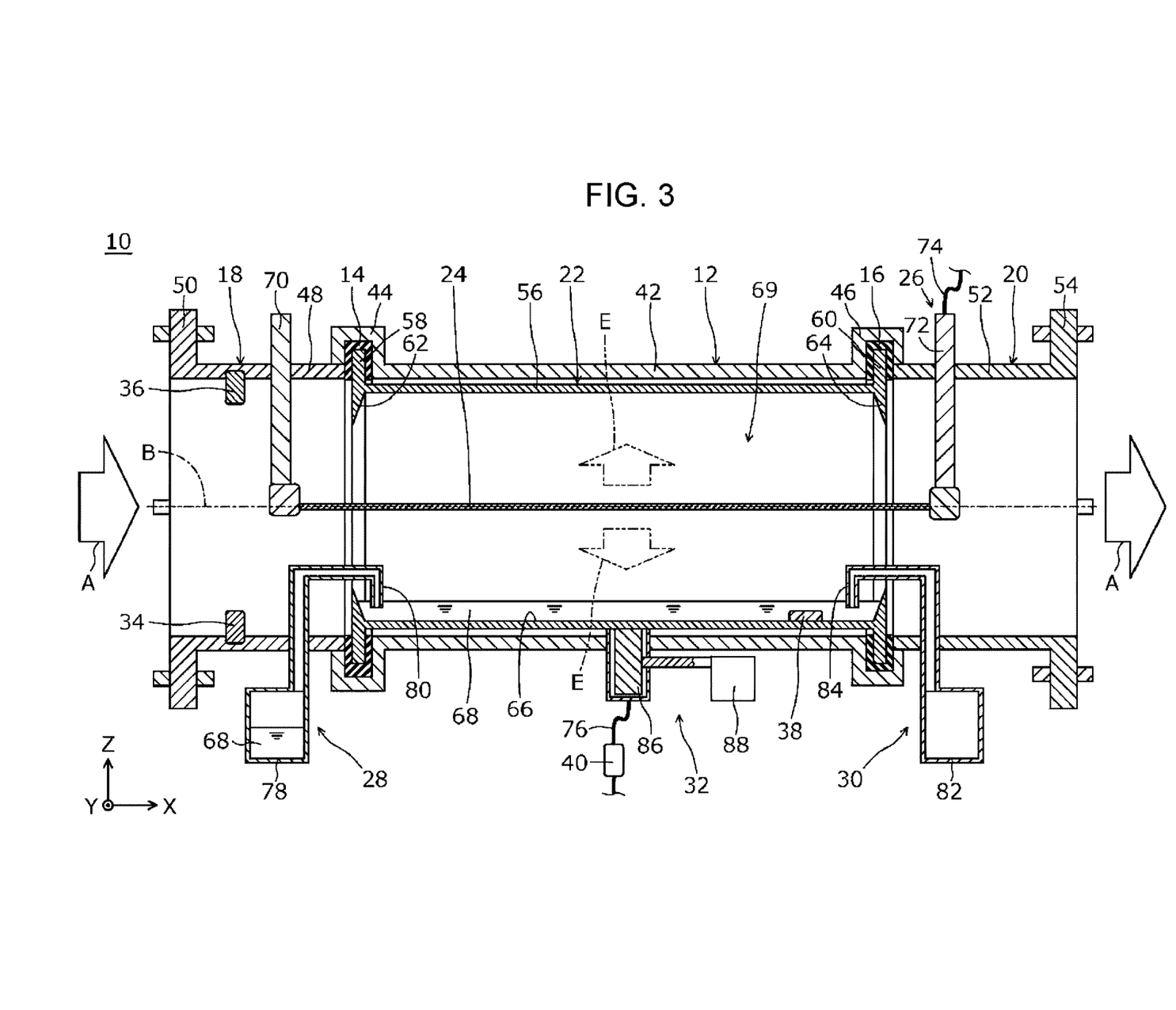
FIG. 3 is a sectional view along line in FIG. 1.
Figure 4:
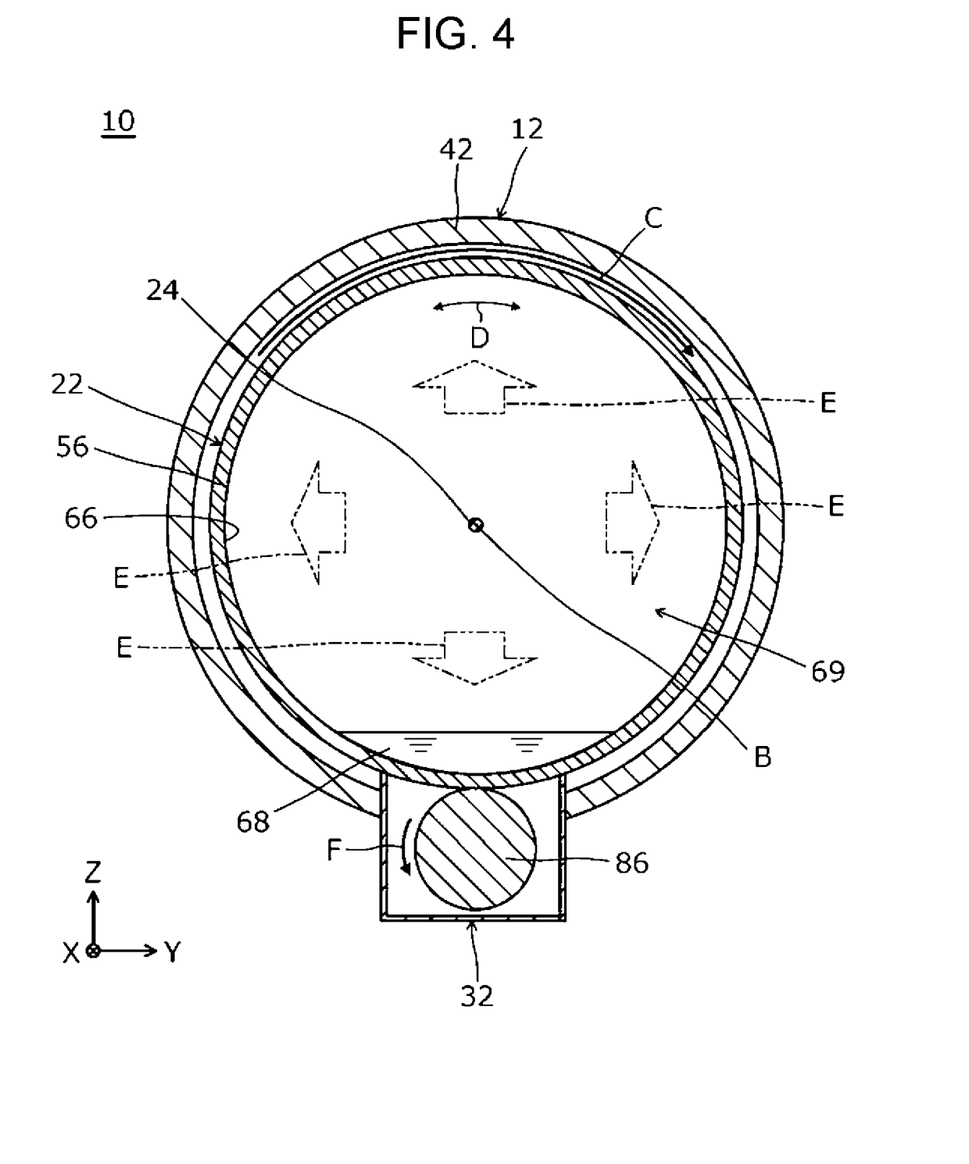
FIG. 4 is an end view along line IV-IV in FIG. 1.
Figure 5:
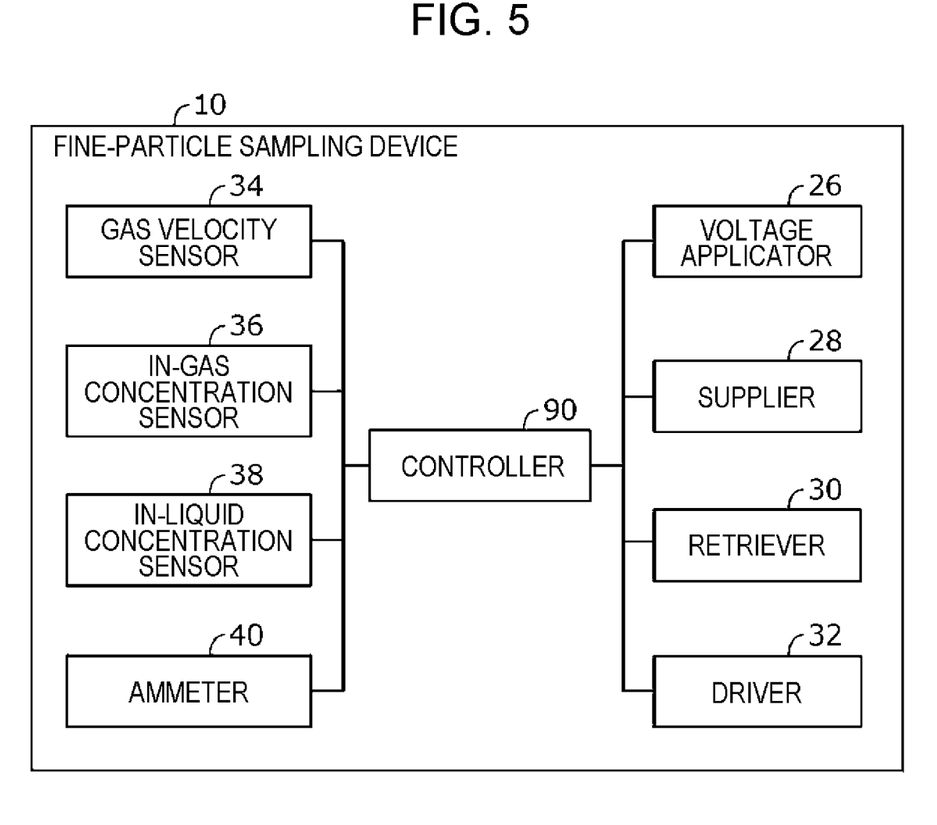
FIG. 5 is a block diagram illustrating a configuration of the fine-particle sampling device in FIG. 1.

FIG. 1 is a perspective view illustrating an appearance of a fine-particle sampling device 10 according to an embodiment. FIG. 2 is a side view illustrating an appearance of the fine-particle sampling device 10 in FIG. 1. FIG. 3 is an internal view of the fine-particle sampling device 10 in FIG. 1 and is a sectional view along line in FIG. 1. FIG. 4 is an end view along line IV-IV in FIG. 1. In FIG. 1, illustrations of a gas velocity sensor 34 and the like are omitted. With reference to FIG. 1 to FIG. 4, the fine-particle sampling device 10 according to an embodiment will be described.

As illustrated in FIG. 1 to FIG. 4, the fine-particle sampling device 10 is a device that samples fine particles in a liquid. Specifically, the fine-particle sampling device 10 is a device that catches fine particles in a gas into a liquid 68 (described later) and thereby samples the fine particles in the liquid. For example, fine particles include fungi, bacteria, viruses, aerosol, and the like. The fine-particle sampling device 10 includes a duct 12, a first bearing seal 14, a second bearing seal 16, a first flange member 18, a second flange member 20, a first electrode 22, a second electrode 24, a voltage applicator 26, a supplier 28, a retriever 30, a driver 32, the gas velocity sensor 34, an in-gas concentration sensor 36, an in-liquid concentration sensor 38, and an ammeter 40.

The fine-particle sampling device 10 is configured such that the first electrode 22 that is rotatable and the second electrode 24 that is disposed at a center portion of the first electrode 22 are surrounded by the duct 12, the first flange member 18, and the second flange member 20. A gas, such as air, is caused to pass through the inside of the fine-particle sampling device 10 in a direction (the direction indicated by the arrows A in FIG. 2) of being inserted into the fine-particle sampling device 10. For example, air may be taken in directly to the inside of the fine-particle sampling device 10 by a pump (not illustrated) or the like to cause a gas to pass through the inside of the fine-particle sampling device 10. Alternatively, for example, with the fine-particle sampling device 10 installed in a device in which a gas such as air flows, for example, in an air-conditioner or an air cleaner, or at a ventilation port or the like, air may be taken in to the inside of the fine-particle sampling device 10 and treated. Thus mounting the fine-particle sampling device 10 on the device that generates a flow of a gas eliminates the need to incorporate a pump or the like for generating a flow of a gas into the fine-particle sampling device 10 and makes it possible to easily realize a small-sized, low-noise, and low-pressure-loss device. Consequently, installation and incorporation are possible at various locations relatively without selecting locations. Hereinafter, each constituent of the fine-particle sampling device 10 will be described.

The duct 12 has a tubular shape and supports the first electrode 22 rotatably in the interior of the duct 12. The duct 12 has a body 42, a first support portion 44, and a second support portion 46. The body 42, the first support portion 44, and the second support portion 46 have insulation properties.

The body 42 has a cylindrical shape, and one end and the other end of the body 42 in the axial direction are open. From the one end of the body 42 in the axial direction, the first support portion 44 projects outward in the radial direction of the body 42 to be integrally formed with the body 42.

The first support portion 44 is recessed outward in the radial direction of the body 42 and has a substantially U-shape (refer to FIG. 3). The first support portion 44 has an annular shape as viewed in the axial direction of the body 42. In the interior of the first support portion 44, the first bearing seal 14 is disposed. The first bearing seal 14 seals between the first support portion 44 and a first outer collar portion 58 (described later) so that a gas does not leak between the first support portion 44 and the first outer collar portion 58. The first support portion 44 supports the first electrode 22 rotatably via the first bearing seal 14. From the other end of the body 42 in the axial direction, the second support portion 46 projects outward in the radial direction of the body 42 to be integrally formed with the body 42. The second support portion 46 is recessed outward in the radial direction of the body 42 and has a substantially U-shape (refer to FIG. 3). The second support portion 46 has an annular shape as viewed in the axial direction of the body 42. In the interior of the second support portion 46, the second bearing seal 16 is disposed. The second bearing seal 16 seals between the second support portion 46 and a second outer collar portion 60 (described later) so that a gas does not leak between the second support portion 46 and the second outer collar portion 60. The second support portion 46 supports the first electrode 22 rotatably via the second bearing seal 16.

The first flange member 18 has a tubular shape and is connected to the duct 12. The first flange member 18 has a body 48 and a flange 50.

The body 48 has a cylindrical shape, and one end and the other end of the body 48 in the axial direction are open. From the one end of the body 48 in the axial direction, the flange 50 projects outward in the radial direction of the body 48 to be integrally formed with the body 48. The flange 50 has an annular shape as viewed in the axial direction of the body 48. The other end of the body 48 in the axial direction is connected to one end of the duct 12 in the axial direction.

The second flange member 20 has a tubular shape and is connected to the duct 12.

The second flange member 20 has a body 52 and a flange 54.

The body 52 has a cylindrical shape, and one end and the other end of the body 52 in the axial direction are open. The one end of the body 52 in the axial direction is connected to the other end of the duct 12 in the axial direction. From the other end of the body 52 in the axial direction, the flange 54 projects outward in the radial direction of the body 52 to be integrally formed with the body 52. The flange 54 has an annular shape as viewed in the axial direction of the body 52.

The first electrode 22 has a tubular shape, and both ends of the first electrode 22 in the axial direction are open. The first electrode 22 is connected to the ground via a second electric wire 76 (described later) and the like. The first electrode 22 has a body 56, the first outer collar portion 58, the second outer collar portion 60, a first inner collar portion 62, and a second inner collar portion 64. For example, the body 56, the first outer collar portion 58, the second outer collar portion 60, the first inner collar portion 62, and the second inner collar portion 64 are formed by using stainless steel, such as SUS.

The body 56 has a cylindrical shape, and one end and the other end of the body 56 in the axial direction are open. The axial direction of the body 56 is a direction (X-axis direction) in which an axis B of the body 56 extends. On the outer peripheral surface of the body 56, the body 56 has external teeth (not illustrated) that mesh with external teeth (not illustrated) of a gear 86 (described later). An inner surface 66 of the body 56 has been subjected to hydrophilic treatment.

The hydrophilic treatment is treatment that processes the inner surface 66 into a fine uneven shape. For example, the hydrophilic treatment is performed by plasma treatment. Alternatively, for example, the hydrophilic treatment is performed by alkali treatment using potassium hydroxide (KOH). To the inner surface 66 of the body 56, a sticking suppression member that suppresses sticking of fine particles is bonded. For example, the sticking suppression member is a blocking agent of skimmed milk, BSA (Bovine Serum Albumin), PEG (Polyethylene Glycol), and the like.

From the one end of the body 56 in the axial direction, the first outer collar portion 58 projects outward in the radial direction of the body 56 to be integrally formed with the body 56. The first outer collar portion 58 has an annular shape around the axis B of the body 56. That is, the first outer collar portion 58 has an annular shape as viewed in the axial direction of the body 56. The first outer collar portion 58 is disposed in the interior of the first bearing seal 14.

From the other end of the body 56 in the axial direction, the second outer collar portion 60 projects outward in the radial direction of the body 56 to be integrally formed with the body 56. The second outer collar portion 60 has an annular shape around the axis B of the body 56. That is, the second outer collar portion 60 has an annular shape as viewed in the axial direction of the body 56. The second outer collar portion 60 is disposed in the interior of the second bearing seal 16.

From the one end of the body 56 in the axial direction, the first inner collar portion 62 projects inward in the radial direction of the body 56 to be integrally formed with the body 56. The first inner collar portion 62 has an annular shape around the axis B of the body 56. That is, the first inner collar portion 62 has an annular shape as viewed in the axial direction of the body 56.

From the other end of the body 56 in the axial direction, the second inner collar portion 64 projects inward in the radial direction of the body 56 to be integrally formed with the body 56. The second inner collar portion 64 has an annular shape around the axis B of the body 56. That is, the second inner collar portion 64 has an annular shape as viewed in the axial direction of the body 56.

The first electrode 22 is installed in an orientation in which the axis B of the body 56 is parallel to the horizontal direction. The first electrode 22 is supported rotatably around the axis B of the body 56 (refer to the arrow C in FIG. 4). In other words, the first electrode 22 is supported to be rotatable on its axis.

The first electrode 22 stores the liquid 68 on the inner surface 66 of the body 56. Specifically, the first electrode 22 stores the liquid 68 at a portion of the inner surface 66 in a direction (refer to the arrow D in FIG. 4) around the axis B of the body 56. The stored liquid 68 is positioned below the axis B of the body 56. At the portion of the inner surface 66, the first electrode 22 stores the liquid 68 in the axial direction of the body 56. The first inner collar portion 62 holds the liquid 68 so that the liquid 68 stored at the portion of the inner surface 66 of the body 56 does not spill from the one end of the body 56 in the axial direction. The second inner collar portion 64 holds the liquid 68 so that the liquid 68 held at the portion of the inner surface 66 of the body 56 does not spill from the other end of the body 56 in the axial direction. As described above, the first electrode 22 stores the liquid 68 at the portion of the inner surface 66 of the body 56 so that the liquid 68 does not flow out to the outside of the body 56. In the inside of the body 56, a space 69 extending through the body 56 in the axial direction is formed above the store liquid 68.

The second electrode 24 has a linear shape and extends in the axial direction of the body 56 of the first electrode 22. The second electrode 24 is inserted into the interior of the body 56 of the first electrode 22 in the radial direction and is positioned in the interior of the body 56. That is, in the axial direction of the body 56, the second electrode 24 projects outward more than the one end of the body 56 and project outward more than the other end of the body 56. The second electrode 24 is disposed to be spaced from the inner surface 66 of the body 56 of the first electrode 22 and disposed in the vicinity of the center of the first electrode 22. The second electrode 24 is disposed in the inside of the space 69. In this embodiment, the second electrode 24 is installed in an orientation in which the axis of the second electrode 24 coincides with the axis B of the body 56 of the first electrode 22. For example, the second electrode 24 is formed of tungsten or the like.

The voltage applicator 26 applies a voltage between the first electrode 22 and the second electrode 24. The voltage applicator 26 has a first support body 70, a second support body 72, a first electric wire 74, and the second electric wire 76.

The first support body 70 is fixed to the first flange member 18 and is positioned in the interior of the first flange member 18. The first support body 70 is connected to one end of the second electrode 24 in the axial direction and supports the second electrode 24. The second support body 72 is fixed to the second flange member 20 and is positioned in the interior of the second flange member 20. The second support body 72 is connected to the other end of the second electrode 24 in the axial direction and supports the second electrode 24. The first support body 70 and the second support body 72 have electrical conductivity and are electrically connected to the second electrode 24. The first electric wire 74 is electrically connected to the second electrode 24 via the second support body 72. The second electric wire 76 is electrically connected to the first electrode 22 via the gear 86 and the like.

The voltage applicator 26 is capable of causing electric power of a selective magnitude and a selective wave form to flow to the first electrode 22 and the second electrode 24 installed in the vicinity of the center of the first electrode 22 through the first electric wire 74 and the second electric wire 76, thereby the fine-particle sampling device 10 performing electrical collection of fine particles. The structure of the second electrode 24 may be not necessarily a linear structure and may be a plate-shaped structure, a needle-shaped structure, or the like. The structure and/or the installation position of the second electrode 24 is not limited as long as being capable of forming a non-uniform electric field. For example, the voltage applicator 26 is realized by a power supply circuit or the like including a convertor and the like. For example, the voltage applicator 26 applies a direct voltage of 6 [kV].

For example, the voltage applicator 26 applies a voltage between the first electrode 22 and the second electrode 24 so that the second electrode 24 side has a higher potential than the first electrode 22 side. Consequently, in the inside of the space 69, an electric field is generated from the second electrode 24 toward the first electrode 22 (refer to the arrows E in FIG. 3 and the arrows E in FIG. 4).

The supplier 28 supplies the liquid 68 to the inside of the first electrode 22 and causes the liquid 68 to be stored at a portion of the inner surface 66 in a direction around the axis B of the first electrode 22. In other words, the supplier 28 supplies the liquid 68 to the inside of the first electrode 22 to cause the liquid 68 to be stored at the portion of the inner surface 66 in the direction around the axis B of the first electrode 22. As described above, the liquid 68 supplied by the supplier 28 is stored on the inner surface 66 of the body 56 of the first electrode 22. The supplier 28 has a tank 78 and an injection portion 80.

The tank 78 holds the liquid 68 that is to be supplied to the inside of the first electrode 22. The liquid 68 held in the tank 78 is discharged through the injection portion 80 by a pump (not illustrated) or the like and is supplied to the inside of the body 56 of the first electrode 22. As described above, the tank 78 for previously storing the liquid 68, such as a catching liquid for sensing an influenza virus, is installed, and the liquid 68 is supplied to the inside of the first electrode 22 through the injection portion 80.

In this embodiment, the supplier 28 supplies as the liquid 68 a liquid for analysis of fine particles. The liquid for analysis of fine particles denotes, for example, a liquid to be used in analysis, a liquid that maintains, for analysis, activity of a target substance included in fine particles, a liquid that applies, for analysis, a mark and the like to a target substance included in fine particles, a liquid that protects, for analysis, a target substance included in fine particles, or a selective combination thereof. For example, when the target substance is an influenza virus, a liquid for the purpose of dissolution and preservation, such as a normal saline solution, a PBS buffer solution, an EDTA buffer solution, and a bicarbonate buffer solution, a liquid including a substance that specifically bonds to the virus and generates magnetism and/or fluorescence, or the like is usable as the liquid 68. The liquid 68 may be not necessarily a liquid for analysis of fine particles and may be, for example, pure water.

The target substance is not limited to an influenza virus. The target substance may be, for example, the other virus and may be a living body (for example, bacteria) other than viruses. The target substance may be not necessarily a living body and may be an environmental pollutant, allergen, or the like.

The retriever 30 retrieves the liquid 68 stored at a portion of the inner surface 66 in the direction around the axis B of the first electrode 22. The retriever 30 has a tank 82 and an extraction portion 84. The liquid 68 stored at the portion of the inner surface 66 in the direction around the axis B of the first electrode 22 is retrieved by being sucked through the extraction portion 84 by a pump (not illustrated) or the like and held in the tank 82. As described above, the liquid 68, such as a catching liquid, in which fine particles are accumulated is sucked through the extraction portion 84 and held in the tank 82.

The driver 32 rotates the first electrode 22 around a rotational axis extending in the axial direction of the body 56 of the first electrode 22 and passing through the inside of the first electrode 22. In this embodiment, the rotational axis coincides with the axis B of the body 56. That is, in this embodiment, the driver 32 rotates the first electrode 22 around the axis B of the body 56 of the first electrode 22. The driver 32 has the gear 86 and a motor 88 for rotating the gear 86. The gear 86 has external teeth (not illustrated) that mesh with external teeth (not illustrated) of the first electrode 22. Rotation (refer to the arrow F in FIG. 4) of the gear 86 by the motor 88 rotates (refer to the arrow C in FIG. 4) the first electrode 22 around the axis B of the body 56. As described above, the first electrode 22 is rotated by the gear 86 driven by the motor 88.

The gas velocity sensor 34 is installed on the inner surface of the body 48 of the first flange member 18 and measures the gas velocity of a gas that passes through the inside of the first electrode 22. A gas outside the fine-particle sampling device 10 passes through the interior of the body 56 of the first electrode 22 through the interior of the first flange member 18 and is discharged to the outside of the fine-particle sampling device 10 through the interior of the second flange member 20 (refer to the arrows A in FIG. 2 and the arrows A in FIG. 3). The gas velocity sensor 34 measures, as described above, the gas velocity of a gas that passes through the inside of the first electrode 22.

The gas outside the fine-particle sampling device 10 may pass through the interior of the body 56 of the first electrode 22 through the interior of the second flange member 20 and be discharged to the outside of the fine-particle sampling device 10 from the first flange member 18. Even in this case, the gas velocity sensor 34 can measure the gas velocity of the gas that passes through the interior of the first electrode 22.

The in-gas concentration sensor 36 is disposed on the inner surface of the body 48 of the first flange member 18 and, as described above, measures the concentration of fine particles in a gas that passes through the inside of the first electrode 22. The in-gas concentration sensor 36 is, for example, an optical sensor.

The in-liquid concentration sensor 38 is disposed in the liquid 68 stored at a portion of the inner surface 66 in the direction around the axis B of the first electrode 22 and measures the concentration of fine particles in the liquid 68. The in-liquid concentration sensor 38 is, for example, an optical sensor.

The ammeter 40 is connected to the second electric wire 76 and measures the current value of current that flows between the first electrode 22 and the second electrode 24. The ammeter 40 may be provided at any location at which the current value of current that flows between the first electrode 22 and the second electrode 24 can be measured.

FIG. 5 is a block diagram illustrating a functional configuration of the fine-particle sampling device 10. With reference to FIG. 5, the functional configuration of the fine-particle sampling device 10 will be described.

As illustrated in FIG. 5, the fine-particle sampling device 10 further includes a controller 90.

The controller 90 is electrically connected to the gas velocity sensor 34, the in-gas concentration sensor 36, the in-liquid concentration sensor 38, the ammeter 40, the voltage applicator 26, the supplier 28, the retriever 30, and the driver 32. The controller 90 controls the voltage applicator 26, the supplier 28, the retriever 30, and the driver 32 on the basis of results of measurement by the gas velocity sensor 34, the in-gas concentration sensor 36, the in-liquid concentration sensor 38, and the ammeter 40. The controller 90 is realized by, for example, a microcomputer and may be realized by a processor or a dedicated circuit.

On the basis of a result of measurement by the gas velocity sensor 34, the controller 90 calculates the flow rate of a gas that passes through the interior of the body 56 of the first electrode 22 and outputs the flow rate. For example, the controller 90 calculates a flow rate by using the gas velocity of the gas that passes through the interior of the body 56 of the first electrode 22 and the sectional area of a flow path through which the gas passes. The controller 90 outputs the calculated flow rate to the other device (not illustrated) or the like. Consequently, it is possible to perform analysis and the like of fine particles by using the flow rate calculated by the controller 90.

The controller 90 controls the voltage applicator 26 and the driver 32 on the basis of a result of measurement by the in-gas concentration sensor 36. Specifically, when the concentration of fine particles in a gas is higher than a predetermined concentration, the controller 90 controls the voltage applicator 26 to apply a voltage to the first electrode 22 and the second electrode 24. In addition, when the concentration of fine particles in a gas is higher than a predetermined concentration, the controller 90 controls the driver 32 to rotate the first electrode 22.

The controller 90 controls the voltage applicator 26 on the basis of a result of measurement by the in-liquid concentration sensor 38. Specifically, when the concentration of fine particles in the stored liquid 68 is higher than a predetermined concentration, the controller 90 controls the voltage applicator 26 to stop application of a voltage by the voltage applicator 26 to the first electrode 22 and the second electrode 24. The controller 90 may control the driver 32 to stop rotation of the first electrode 22, for example, when the concentration of fine particles in the stored liquid 68 is higher than a predetermined concentration. Alternatively, the controller 90 may control the retriever 30 to retrieve the stored liquid 68, for example, when the concentration of fine particles in the stored liquid 68 is higher than a predetermined concentration.

The controller 90 controls the supplier 28 on the basis of a result of measurement by the ammeter 40. For example, when the liquid amount of the stored liquid 68 is decreased, resistance is decreased and the value of current that flows between the first electrode 22 and the second electrode 24 is increased. Thus, the controller 90 controls the supplier 28, when the value of current measured by the ammeter 40 is larger than a predetermined value, to supply the liquid 68 to the inside of the body 56 of the first electrode 22 and replenish the inside of the body 56 of the first electrode 22 with the liquid 68.

Figure 6:
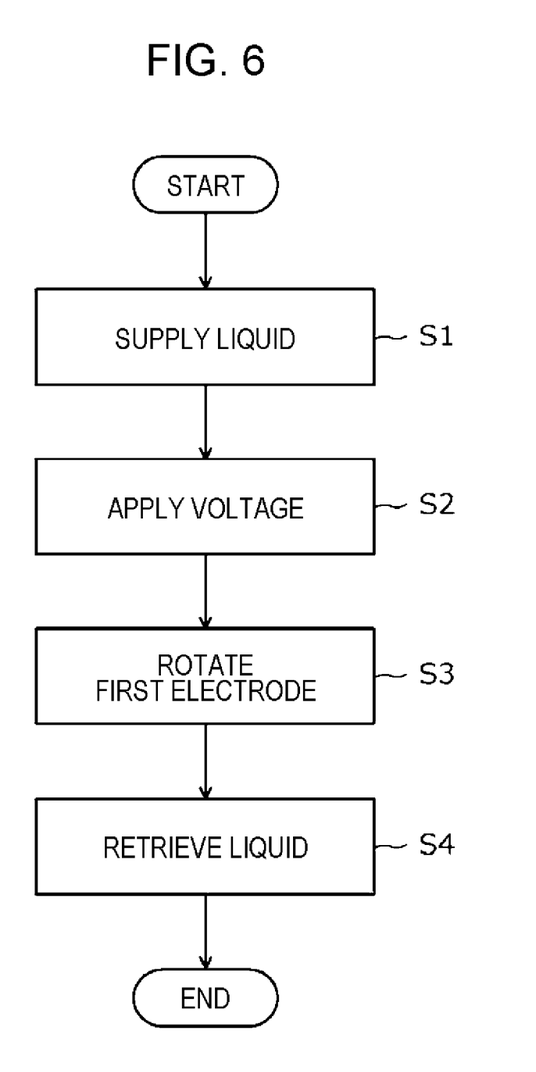
FIG. 6 is a flow chart illustrating one example of an operation of the fine-particle sampling device in FIG. 1.
Figure 7:
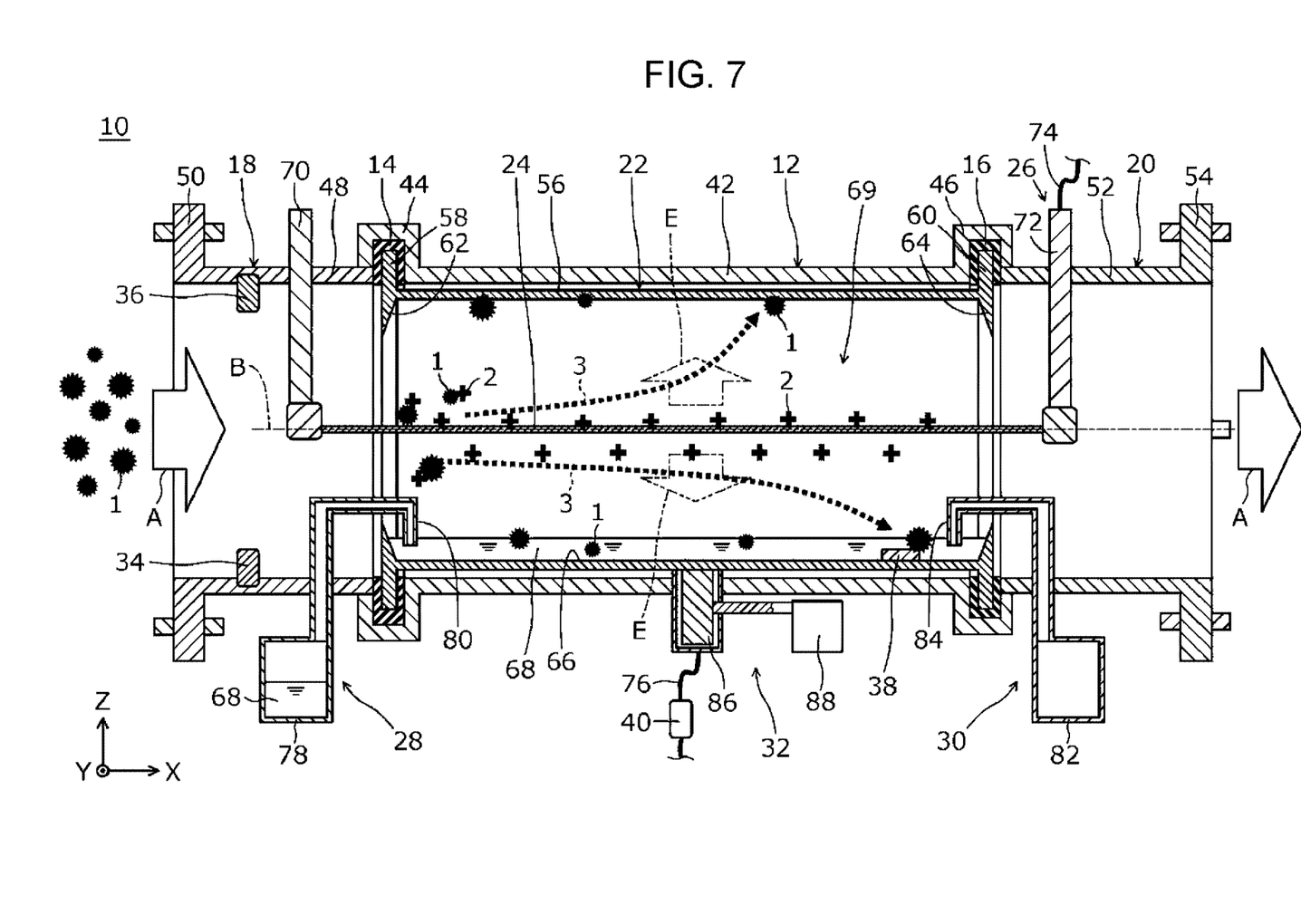
FIG. 7 is a sectional view along line VII-VII in FIG. 1 and an explanatory view for describing one example of an operation performed by the fine-particle sampling device in FIG. 1.

Next, an operation of the fine-particle sampling device 10 configured as described above will be described. FIG. 6 is a flow chart illustrating one example of the operation of the fine-particle sampling device 10. FIG. 7 is an explanatory view for describing one example of the operation of the fine-particle sampling device 10 and is a view illustrating a movement of a virus in the inside of the fine-particle sampling device 10 until the virus is actually retrieved. With reference to FIG. 6 and FIG. 7, one example of the operation of the fine-particle sampling device 10, including a flow of catching an influenza virus 1, retrieving the influenza virus 1 in a liquid, and retrieving the liquid 68, in the present embodiment will be described. Here, the fine-particle sampling device 10 catches the influenza virus 1 in a liquid for the purpose of retrieving the influenza virus 1, with which airborne infection is considered to occur, as a liquid sample that can be analyzed by a sensor or the like.

As illustrated in FIG. 6, first, the supplier 28 supplies the liquid 68 to the inside of the first electrode 22 and causes the liquid 68 to be stored at a portion of the inner surface 66 in the direction around the axis B of the first electrode 22 (supply step) (step S1). For example, by a user operating a selective operation button (not illustrated) or the like, the supplier 28 is operated to supply the liquid 68 to the inside of the body 56 of the first electrode 22. The liquid 68 may be supplied to the inside of the body 56 of the first electrode 22, for example, by the controller 90 controlling the supplier 28 on the basis of a result of measurement by the in-gas concentration sensor 36.

As illustrated in FIG. 7, the liquid 68 is supplied to the inside of the body 56 of the first electrode 22, and the liquid 68 is stored at a portion of the inner surface 66 in the direction around the axis B of the body 56 of the first electrode 22.

Refer back to FIG. 6, next, the voltage applicator 26 applies a voltage between the first electrode 22 and the second electrode 24 (voltage application step) (step S2). For example, by the controller 90 controlling the voltage applicator 26 on the basis of a result of measurement by the in-gas concentration sensor 36, a voltage is applied between the first electrode 22 and the second electrode 24. Alternatively, for example, a voltage may be applied between the first electrode 22 and the second electrode 24 by a user operating a selective operation button (not illustrated) or the like to operate the voltage applicator 26.

As illustrated in FIG. 7, the influenza virus 1 in a gas introduced to the inside of the fine-particle sampling device 10 by a selective air flow (refer to the arrows A in FIG. 7) is first electrically charged positively or negatively by an ion 2 discharged due to electric discharge of the second electrode 24 to which a high voltage has been applied. Here, a case in which the influenza virus 1 is electrically charged positively will be described. The influenza virus 1 in an electrified (charged) state moves as a track 3 indicates due to an electric field (refer to the arrows E in FIG. 7) formed between the second electrode 24 and the first electrode 22 and is collected at the inner surface 66 of the first electrode 22. As described above, the influenza virus 1 adheres to the inner surface 66 of the first electrode 22 and is caught on the inner surface 66.

Refer back to FIG. 6, next, the driver 32 rotates the first electrode 22 around the axis B (drive step) (step S3). For example, by the controller 90 controlling the driver 32 on the basis of a result of measurement by the in-gas concentration sensor 36, the first electrode 22 is rotated. Alternatively, for example, the first electrode 22 may be rotated by a user operating a selective operation button (not illustrated) or the like to operate the driver 32.

As illustrated in FIG. 7, the first electrode 22 rotates around the axis B in a state in which the liquid 68 is stored at a portion of the inner surface 66 in the direction around the axis B of the body 56 of the first electrode 22. In other words, the first electrode 22 rotates around the axis B in a state of storing the liquid 68 below the axis B so that the liquid 68 does not flow out to the outside of the body 56. Consequently, the inner surface 66 of the first electrode 22 sequentially comes into contact with the stored liquid 68.

The influenza virus 1 collected on the inner surface 66 is retrieved at a selective timing by the liquid 68 stored in the inside of the body 56 of the first electrode 22. Specifically, the influenza virus 1 adhering to the inner surface 66 of the body 56 of the first electrode 22 is retrieved in the liquid 68 by coming into contact with the stored liquid 68 and thereby separating from the inner surface 66. With the movement (rotation) of the first electrode 22 that is rotated by the motor 88 and the gear 86, it becomes possible to wash the entire surface of the inner surface 66 of the first electrode 22 with the accumulated (stored) liquid 68.

A voltage may be applied between the first electrode 22 and the second electrode 24 in a state in which the first electrode 22 is rotated around the axis B by previously rotating the first electrode 22 around the axis B before the voltage is applied between the first electrode 22 and the second electrode 24.

Refer back to FIG. 6, last, the retriever 30 retrieves the stored liquid 68 (retrieve step) (step S4). For example, the liquid 68 can be retrieved into the retriever 30 (tank 82) through the extraction portion 84 at a selective timing after a certain time of operation, and a liquid sample (liquid 68) that includes the influenza virus 1 separated from a gas can be obtained. The liquid 68 stored in the inside of the body 56 of the first electrode 22 may be retrieved by, for example, the controller 90 controlling the retriever 30 on the basis of a result of measurement by the in-liquid concentration sensor 38. Alternatively, for example, the liquid 68 stored in the inside of the body 56 of the first electrode 22 may be retrieved by a user operating a selective operation button (not illustrated) or the like to operate the retriever 30.

By using the gas velocity sensor 34, the in-gas concentration sensor 36, and the in-liquid concentration sensor 38 when performing sampling of fine particles, it is possible to perform sampling more appropriately and efficiently. By combining information on operation time with gas velocity information obtained by the gas velocity sensor 34 and area information at a place of measurement by the gas velocity sensor 34, it is possible to obtain information on the amount of a processed air volume. From the in-gas concentration sensor 36, information on the concentration of fine particles included in sucked air can be obtained. From the in-liquid concentration sensor 38, information on the concentration of fine particles included in the stored liquid 68 can be obtained. By using these sensors, it is possible to set operation time of start and stop of sampling of fine particles and/or timing of start and stop of operation to conditions desired by a user. For example, examples of conditions are "start operation as air in which the particle concentration is $10000/cm^3$ has come", "end operation as air of 1 $m^3$ has been processed", "end operation as 1000/mL has been achieved", and the like, and it is possible to select optimum sampling in accordance with intended use of sampling.

By adding a function of reading current at the same time when applying a high voltage, it is possible to suppress supply of the liquid 68 more than necessary and possible to suppress depletion of the liquid 68. Specifically, a current value measured by the ammeter 40 is read, and, when the current value is more than a predetermined threshold value, the liquid 68 of a minimum amount is supplied by the supplier 28 to the inside of the body 56 of the first electrode 22. Consequently, it is possible to keep the concentration of fine particles in the stored liquid 68 to be in a high concentration state, as much as possible.

As described above, the fine-particle sampling device 10 according to the present embodiment is capable of retrieving the influenza virus 1 at high concentration from air in the liquid 68. In addition, by combining information obtained from various sensors, it is possible to perform sampling efficiently and possible to perform sampling under optimum conditions in accordance with a purpose of use by a user.

The fine-particle sampling device 10 may retrieve aerosol including an influenza virus from air into the liquid 68 under a classification by particle diameter range of two types. Consequently, it is possible to analyze the amount of the influenza virus in each particle diameter range.

The fine-particle sampling device 10 can accumulate fine particles in the liquid 68 stored in the inside of the first electrode 22 without circulating the liquid 68. Thus, it is easy to retrieve the liquid 68 such that the concentration of the fine particles in the liquid 68 is high concentration. The fine-particle sampling device 10 is a device that does not need provision of an instrument or the like for circulating the liquid 68 and that can easily achieve downsizing and energy saving.

As described above, the fine-particle sampling device 10 according to the present embodiment is a fine-particle sampling device that samples fine particles in a liquid. The fine-particle sampling device includes the first electrode 22 having a tubular shape and whose both ends in the axial direction thereof are open; the second electrode 24 extending in the axial direction of the first electrode 22 and disposed in the inside of the first electrode 22 to be spaced from the inner surface 66 of the first electrode 22; the supplier 28 that supplies the liquid 68 to the inside of the first electrode 22 and causes the liquid 68 to be stored at a portion of the inner surface 66 in the direction around the axis B of the first electrode 22; the voltage applicator 26 that applies a voltage between the first electrode 22 and the second electrode 24; the driver 32 that rotates the first electrode 22 around the rotational axis extending in the axial direction of the first electrode 22 and passing through the inside of the first electrode 22; and the retriever 30 that retrieves the stored liquid 68.

According to this, by the voltage applicator 26 applying a voltage between the first electrode 22 and the second electrode 24, an electric field is generated between the first electrode 22 and the second electrode 24, and fine particles in a gas in the inside of the first electrode 22 adhere to the inner surface 66 of the first electrode 22. By the driver 32 rotating the first electrode 22, the inner surface 66 of the first electrode 22 is sequentially caused to come into contact with the liquid 68 stored at a portion of the inner surface 66 in the direction around the axis B of the body 56, and the fine particles adhering to the inner surface 66 are accumulated in the liquid 68. As a result of the retriever 30 retrieving the stored liquid 68, the liquid 68 in which the fine particles are accumulated is obtained. Since the fine particles thus guided as described above to the inside of the fine-particle sampling device 10 are accumulated in the liquid 68 due to rotation of the first electrode 22 after deposited on the inner surface 66 of the first electrode 22 due to electrical collection, it is possible to sample the fine particles efficiently. It is also possible to reduce the liquid amount of the liquid 68 since there is no need to circulate the liquid 68. By thus accumulating the fine particles in the liquid 68 of a small liquid amount, it is possible to easily cause the concentration of the fine particles in the liquid 68 to be a high concentration and possible to sample the fine particles efficiently.

The fine-particle sampling device 10 according to the present embodiment further includes the gas velocity sensor 34 that measures the gas velocity of a gas that passes through the inside of the first electrode 22.

According to this, it is possible to measure the gas velocity of a gas that passes through the inside of the first electrode 22 and thus possible to easily determine whether a gas flows in the inside of the first electrode 22. For example, by performing application of a voltage or the like when a gas flows in the inside of the first electrode 22, fine particles are easily caught. It is thus possible to more efficiently sample the fine particles. As described above, it is possible to adjust time and timing to apply a voltage between the first electrode 22 and the second electrode 24, timing to end voltage application, timing to start retrieve of the liquid 68, and the like in accordance with gas velocity information from the gas velocity sensor 34. Consequently, it is possible to easily perform sampling at timing and operation time that are optimum and appropriate in accordance with an intended use of the sampling.

The fine-particle sampling device 10 according to the present embodiment further includes the controller 90 that calculates the flow rate of a gas on the basis of a result of measurement by the gas velocity sensor 34 and outputs the flow rate.

According to this, it is possible to adjust timing to end voltage application, timing to start retrieve of the liquid 68, and the like on the basis of the flow rate of a gas that has passed through the inside of the first electrode 22 and possible to sample fine particles more efficiently.

The fine-particle sampling device 10 according to the present embodiment further includes the in-gas concentration sensor 36 that measures the concentration of fine particles in a gas that passes through the inside of the first electrode 22. The controller 90 controls the voltage applicator 26 and the driver 32 on the basis of a result of measurement by the in-gas concentration sensor 36.

According to this, fine particles in a gas are easily collected by applying a voltage and rotating the first electrode 22 when a concentration higher than a predetermined concentration has been measured. By thus performing operation when a gas of a desired fine-particle concentration is introduced, it is possible to sample fine particles more efficiently.

The fine-particle sampling device 10 according to the present embodiment further includes the in-liquid concentration sensor 38 that measures the concentration of fine particles in the stored liquid 68. The controller 90 causes the voltage applicator 26 to stop application of a voltage when the concentration of the fine particles in the liquid 68 is higher than a predetermined concentration.

According to this, when the concentration of the fine particles in the liquid 68 has become higher than a predetermined concentration as a result of the fine particles being accumulated in the liquid 68, sampling can be ended by stopping application of a voltage. Accordingly, it is possible to avoid sampling time from unnecessarily lengthening and the concentration of the fine particles in the liquid 68 from becoming thin and not possible to be analyzed, and it is possible to sample the fine particles more efficiently.

The fine-particle sampling device 10 according to the present embodiment further includes the ammeter 40 that measures the value of current that flows between the first electrode 22 and the second electrode 24. The controller 90 causes the supplier 28 to replenish the inside of the first electrode 22 with the liquid 68 when the value of the current is larger than a predetermined value.

According to this, the value of current that flows between the first electrode 22 and the second electrode 24 can be measured, and, when the value of the current is larger than a predetermined value, the supplier 28 replenishes the inside of the first electrode 22 with the liquid 68. For example, replenishment with a predetermined amount of the liquid 68 can be performed when the liquid amount of the liquid 68 has decreased with a lapse of time and the value of the current has become larger than a predetermined value. Consequently, it is possible to suppress a decrease in the concentration of fine particles as a result of the liquid amount of the liquid 68 stored in the inside of the first electrode 22 being increased more than necessary and possible to suppress depletion of the liquid 68. It is thus possible to sample fine particles more efficiently.

In the fine-particle sampling device 10 according to the present embodiment, the inner surface 66 of the first electrode 22 has been subjected to hydrophilic treatment.

According to this, when fine particles that adhere to the inner surface 66 come into contact with the stored liquid 68, the fine particles easily separate from the inner surface 66. It is thus possible to suppress a loss during retrieve of fine particles collected on the inner surface 66 and possible to sample fine particles more efficiently.

In the fine-particle sampling device 10 according to the present embodiment, the sticking suppression member that suppresses sticking of fine particles is bonded to the inner surface 66 of the first electrode 22.

According to this, when fine particles that adhere to the inner surface 66 come into contact with the stored liquid 68, the fine particles easily separate from the inner surface 66. It is thus possible to suppress a loss during retrieve of fine particles collected on the inner surface 66 and possible to sample fine particles more efficiently.

In the fine-particle sampling device 10 according to the present embodiment, the supplier 28 supplies as the liquid 68 a liquid for analysis of fine particles.

According to this, it is possible to easily extract a target substance or the like included in fine particles. In addition, by selecting the liquid 68 that is suitable in accordance with an object and/or intended use, it is possible to address execution of an appropriate detection protocol and/or avoiding of damage to a sample, and the like.

OTHER EMBODIMENTS

In the above-described embodiment, a case in which the body 56 of the first electrode 22 has a cylindrical shape has been described. However, the body 56 is not limited thereto. For example, the body of the first electrode may be an elliptic cylinder, a polygonal cylinder, or the like.

In the above-described embodiment, a case in which the first electrode 22 is installed in an orientation in which the axis B of the body 56 is parallel to the horizontal direction has been described. However, the first electrode 22 is not limited thereto and may be not necessarily installed in an orientation in which the axis B of the body 56 is parallel to the horizontal direction. For example, the first electrode 22 may be installed in an orientation in which the axis B of the body 56 is inclined with respect to the horizontal direction as long as being capable of storing the liquid 68 at a portion of the inner surface 66 in the direction around the axis B of the body 56 so that the liquid 68 does not flow out to the outside of the body 56. In other words, the first electrode 22 may be disposed in any orientation in which the liquid 68 can be stored on the inner surface 66.

In the above-described embodiment, a case in which the second electrode 24 is installed in an orientation in which the axis of the second electrode 24 coincides with the axis B of the body 56 of the first electrode 22 has been described. However, the second electrode 24 is not limited thereto and may be not necessarily installed in an orientation in which the axis of the second electrode 24 coincides with the axis B of the body 56 of the first electrode 22. For example, the second electrode 24 may be installed in an orientation in which the axis of the second electrode 24 is inclined with respect to the axis B of the body 56 as long as at least extending in the axial direction of the body 56 of the first electrode 22. Alternatively, for example, the second electrode 24 may be installed in an orientation in which the axis of the second electrode 24 does not coincide with the axis B of the body 56 of the first electrode 22 and the axis of the second electrode 24 is parallel to the axis B of the body 56 of the first electrode 22.

In the above-described embodiment, a case in which the second electrode 24 has a linear shape has been described. However, the second electrode 24 is not limited thereto. For example, the second electrode may have a plate shape, a needle shape, or the like.

In the above-described embodiment, a case in which one second electrode 24 is disposed in the inside of the first electrode 22 has been described. However, the second electrode is not limited thereto. For example, second electrodes may be disposed in the inside of the first electrode.

In the above-described embodiment, a case in which the second electrode 24 projects outward more than one end of the body 56 and projects outward more than the other end of the body 56 has been described. However, the second electrode 24 is not limited thereto. For example, the length of the second electrode 24 may be the same as the length of the body 56 and may be shorter than the length of the body 56.

In the above-described embodiment, the driver 32 rotates the first electrode 22 around the axis B of the body 56 of the first electrode 22 has been described. However, the driver 32 is not limited thereto. For example, the driver may rotate the first electrode around a rotational axis slightly inclined with respect to the axis of the body of the first electrode. Alternatively, the driver may rotate the first electrode around a rotational axis parallel to the axis of the body of the first electrode. It is sufficient for the driver to rotate the first electrode around a rotational axis extending in the axial direction of the first electrode and passing through the inside of the first electrode.

The present disclosure is widely usable for a device that samples fine particles of aerosol or the like from a gas, such as air.

What is claimed is:

1. A fine-particle sampling device that samples fine particles in a liquid, the fine-particle sampling device comprising:
   a first electrode having a tubular shape and whose both ends in an axial direction thereof are open;
   a second electrode extending in the axial direction of the first electrode and disposed in an inside of the first electrode to be spaced from an inner surface of the first electrode;
   a supplier that supplies a liquid to the inside of the first electrode and causes the liquid to be stored at a portion of the inner surface in a direction around an axis of the first electrode;
   a voltage applicator that applies a voltage between the first electrode and the second electrode;
   a driver that rotates the first electrode around a rotational axis extending in the axial direction of the first electrode and passing through the inside of the first electrode; and
   a retriever that retrieves the stored liquid.

2. The fine-particle sampling device according to claim 1, further comprising:
   a gas velocity sensor that measures a gas velocity of a gas that passes through the inside of the first electrode.

3. The fine-particle sampling device according to claim 2, further comprising:
   a controller that calculates a flow rate of the gas based on a result of measurement by the gas velocity sensor and outputs the flow rate.

4. The fine-particle sampling device according to claim 3, further comprising:
   an in-gas concentration sensor that measures a concentration of the fine particles in the gas that passes through the inside of the first electrode,
   wherein the controller controls the voltage applicator and the driver based on a result of measurement by the in-gas concentration sensor.

5. The fine-particle sampling device according to claim 3, further comprising:
   an in-liquid concentration sensor that measures a concentration of the fine particles in the stored liquid,
   wherein the controller causes the voltage applicator to stop application of a voltage when the concentration of the fine particles in the liquid is higher than a predetermined concentration.

6. The fine-particle sampling device according to claim 3, further comprising:
   an ammeter that measures a value of current that flows between the first electrode and the second electrode,
   wherein the controller causes the supplier to replenish the inside of the first electrode with the liquid when the value of the current is larger than a predetermined value.

7. The fine-particle sampling device according to claim 1, wherein the inner surface of the first electrode has been subjected to hydrophilic treatment.

8. The fine-particle sampling device according to claim 1, wherein a sticking suppression member that suppresses sticking of the fine particles is bonded to the inner surface of the first electrode.

9. The fine-particle sampling device according to claim 1, wherein the supplier supplies, as the liquid, a liquid for analysis of the fine particles.

10. A method of sampling fine-particles by using a first electrode having a tubular shape and whose both ends in an axial direction thereof are open, and a second electrode extending in the axial direction of the first electrode and disposed in an inside of the first electrode to be spaced from an inner surface of the first electrode, the method comprising:
    supplying a liquid to the inside of the first electrode and causing the liquid to be stored at a portion of the inner surface in a direction around an axis of the first electrode;
    applying a voltage between the first electrode and the second electrode;
    driving by rotating the first electrode around a rotational axis extending in the axial direction of the first electrode and passing through the inside of the first electrode; and
    retrieving the stored liquid.

11. A fine-particle sampling device comprising:
    a first electrode including a tubular portion provided around a first imaginary axis, a first end of the tubular portion, and a second end of the tubular portion, the first end having a first hole, the second end having a second hole;
    a second electrode having a first part, the first part being included in a first space, the first space being defined by the tubular portion, the first end, and the second end, the second electrode having a longitudinal direction that coincides with an axial direction of the first imaginary axis;
    a supply device that supplies a liquid to the first space, the liquid being in contact with a part of a surface of the tubular portion;
    a voltage application device that applies a voltage between the first electrode and the second electrode to cause fine particles included in a gas included in the first space to move toward the surface;
    a driver that rotates the first electrode around the first imaginary axis, the liquid moving on the surface, the liquid catching fine particles in a vicinity of the surface; and
    a retriever that retrieves the liquid including the caught fine particles.

* * * * *